United States Patent
Zhou

(10) Patent No.: US 10,441,633 B2
(45) Date of Patent: Oct. 15, 2019

(54) USES OF NEUREGULIN IN PREVENTING, TREATING OR DELAYING VENTRICULAR ARRHYTHMIA, AND COMPOSITION THEREOF

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

(21) Appl. No.: 15/513,939

(22) PCT Filed: Sep. 6, 2015

(86) PCT No.: PCT/CN2015/088972
§ 371 (c)(1),
(2) Date: Mar. 23, 2017

(87) PCT Pub. No.: WO2016/045493
PCT Pub. Date: Mar. 31, 2016

(65) Prior Publication Data
US 2017/0368140 A1 Dec. 28, 2017

(30) Foreign Application Priority Data
Sep. 24, 2014 (CN) .......................... 2014 1 0529437

(51) Int. Cl.
| | | |
|---|---|---|
| A61K 38/16 | (2006.01) | |
| A61K 38/18 | (2006.01) | |
| C07K 14/475 | (2006.01) | |
| A61K 38/17 | (2006.01) | |
| A61K 45/06 | (2006.01) | |
| A61P 9/06 | (2006.01) | |

(52) U.S. Cl.
CPC .......... *A61K 38/1883* (2013.01); *A61K 38/17* (2013.01); *A61K 45/06* (2013.01); *A61P 9/06* (2018.01)

(58) Field of Classification Search
None
See application file for complete search history.

(56) References Cited

U.S. PATENT DOCUMENTS

| | | | |
|---|---|---|---|
| 5,530,109 A | 6/1996 | Goodearl et al. | |
| 5,716,930 A | 2/1998 | Goodearl et al. | |
| 5,834,229 A | 11/1998 | Vandlen et al. | |
| 6,444,642 B1 | 9/2002 | Sklar et al. | |
| 7,226,907 B1 | 6/2007 | Zhou | |
| 7,612,164 B2 | 11/2009 | Zhou | |
| 7,795,212 B2 | 9/2010 | Zhou | |
| 7,964,555 B2 | 6/2011 | Zhou | |
| 8,476,405 B2 | 7/2013 | Zhou | |
| 8,609,620 B2 | 12/2013 | Zhou | |
| 8,785,387 B2 | 7/2014 | Zhou | |
| 9,012,400 B2 | 4/2015 | Zhou | |
| 9,089,524 B2 | 7/2015 | Zhou | |
| 9,340,597 B2 | 5/2016 | Zhou | |
| 9,434,777 B2 | 9/2016 | Zhou | |
| 9,555,076 B2 | 1/2017 | Zhou | |
| 9,580,515 B2 | 2/2017 | Zhou | |
| 9,655,949 B2 | 5/2017 | Zhou | |
| 10,098,834 B2 | 10/2018 | Zhou | |
| 10,112,983 B2 | 10/2018 | Zhou | |
| 2006/0199767 A1 | 9/2006 | Zhou | |
| 2007/0129296 A1 | 6/2007 | Zhou | |
| 2007/0190127 A1 | 8/2007 | Zhou | |
| 2007/0213264 A1 | 9/2007 | Zhou | |
| 2009/0156488 A1 | 6/2009 | Zhou | |
| 2011/0229444 A1 | 9/2011 | Zhou | |
| 2013/0078235 A1 | 3/2013 | Zhou | |
| 2013/0196911 A1 | 8/2013 | Jay et al. | |
| 2014/0364366 A1 | 12/2014 | Zhou | |
| 2015/0284440 A1 | 10/2015 | Zhou | |
| 2016/0095903 A1 | 4/2016 | Zhou | |
| 2016/0324876 A1 | 11/2016 | Zhou | |
| 2017/0007671 A1 | 1/2017 | Zhou | |
| 2017/0189489 A1 | 7/2017 | Zhou | |
| 2017/0232068 A1 | 8/2017 | Zhou | |
| 2017/0313784 A1 | 11/2017 | Zhou | |
| 2017/0326204 A1 | 11/2017 | Zhou | |
| 2017/0360889 A1 | 12/2017 | Zhou | |

FOREIGN PATENT DOCUMENTS

| | | |
|---|---|---|
| CN | 1138785 C | 2/2004 |
| CN | 101310766 A | 11/2008 |
| WO | WO 1994/26298 A1 | 11/1994 |

(Continued)

OTHER PUBLICATIONS

Wang et al., Improvement of cardiac function and reversal of gap junction remodeling by Neuregulin-1β in volume-overloaded rats with heart failure. Journal of Geriatric Cardiology (2012) 9: 172-179 (Year: 2012).*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Carraway et al., "Neuregulin-2, a new ligand of ErbB/ErbB4-receptor tyrosine kinase," *Nature*, 387:512-516 (1997).
Chang et al., "Ligands for ErbB-family receptors encoded by a neuregulin-like gene," *Nature*, 387:509-512 (1997).
Falls et al. "Neuregulins: functions, forms, and signaling strategies," *Exp. Cell Res.*, 284(1):14-30 (2003).

(Continued)

*Primary Examiner* — Christine J Saoud
*Assistant Examiner* — Jon M Lockard
(74) *Attorney, Agent, or Firm* — Jones Day

(57) ABSTRACT

Disclosed are uses of neuregulin in the preparation of medicines for preventing, treating or delaying ventricular arrhythmia of a human being, and pharmaceutical preparations that comprise the neuregulin and are used for preventing, treating or delaying the ventricular arrhythmia.

16 Claims, 7 Drawing Sheets

Specification includes a Sequence Listing.

(56) References Cited

FOREIGN PATENT DOCUMENTS

| WO | WO 97/09425 A1 | 3/1997 |
|---|---|---|
| WO | WO 99/18976 A1 | 4/1999 |
| WO | WO 00/37095 A1 | 6/2000 |
| WO | WO 00/64400 A2 | 11/2000 |
| WO | WO 00/78347 A1 | 12/2000 |
| WO | WO 03/099300 A1 | 12/2003 |
| WO | WO 03/099320 A1 | 12/2003 |
| WO | WO 03/099321 A1 | 12/2003 |
| WO | WO 2007/062594 A1 | 6/2007 |
| WO | WO 2007/076701 A1 | 7/2007 |
| WO | WO 2008/028405 A1 | 3/2008 |
| WO | WO 2009/033373 A1 | 3/2009 |
| WO | WO 2010/060265 A1 | 6/2010 |
| WO | WO 2010/060266 A1 | 6/2010 |
| WO | WO 2010/142141 A1 | 12/2010 |
| WO | WO 2011/091723 A1 | 8/2011 |
| WO | WO 2013/053076 A1 | 4/2013 |
| WO | WO 2013/053158 A1 | 4/2013 |
| WO | WO 2013/053201 A1 | 4/2013 |
| WO | WO 2014/056121 A1 | 4/2014 |
| WO | WO 2014/187342 A1 | 11/2014 |
| WO | WO 2015/101182 A1 | 7/2015 |
| WO | WO2015/101208 A1 | 7/2015 |
| WO | WO2016/058493 A1 | 4/2016 |

OTHER PUBLICATIONS

Higashiyama et al., "A novel brain-derived member of the epidermal growth factor family that interacts with ErbB3 and ErbB4," *J. Biochem.*, 122:675-680 (1997).

Hijazi et al., "NRG-3 in human breast cancers: activation of multiple erbB family proteins," *Int. J. Oncol.*, 13:1061-1067 (1998).

Holmes et al., "Identification of heregulin, a specific activator of $p185^{erbB2}$," *Science*, 256:1205-1210 (1992).

Wang et al., "Improvement of cardiac function and reversal of gap junction remodeling by Neuregulin-1β in volume-overloaded rats with heart failure," *J Geriatr. Cardiol.*, 9(2):172-179 (2012).

Watson et al., *Molecular Biology of the Gene*, $4^{th}$ Edition, The Bejacmin/Cummings Publishing Company, Inc., Menlo Park, CA, p. 224 (1987).

Yarden et al., "Untangling the ErbB signaling network," *Nat. Rev. Mol. Cell Biol.*, 2(2):127-137 (2001).

Zhao et al., "Neuregulins promote survival and growth of cardiac myocytes. Persistence of ErbB2 and ErbB4 expression in neonatal and adult ventricular myocytes," *J Biol. Chem.*, 273(17):10261-10269 (1998).

\* cited by examiner

USES OF NEUREGULIN IN PREVENTING, TREATING OR DELAYING VENTRICULAR ARRHYTHMIA, AND COMPOSITION THEREOF

This application is a U.S. National Stage of International Application No. PCT/CN2015/088972, filed Sep. 6, 2015, which claims priority to Chinese application No. 201410529437.4, filed Sep. 24, 2014, each of which is incorporated herein by reference in their entirety.

This application incorporates by reference a Sequence Listing with this application as an ASCII text file entitled "11748-072-999_SL.TXT" created on Aug. 14, 2017, and having a size of 1,648 bytes.

FIELD OF THE INVENTION

The present invention relates to the use of neuregulin protein in the preparation of a medicament for preventing, treating or delaying ventricular arrhythmias in a human and methods for preventing, treating or delaying ventricular arrhythmias in humans using said medicament. Particularly, the present invention provides methods for preventing, treating or delaying ventricular arrhythmias, comprising administering a medicament comprising a neuregulin protein to a patient who has had or at high risk of ventricular arrhythmias. Specially, this invention relates to a new indication of neuregulin in treatment of cardiovascular disease, i.e., anti-ventricular arrhythmia.

BACKGROUND OF THE INVENTION

Neuregulin (NRG; heregulin, HRG), also known as glial growth factor (GGF) and new differentiation factor (NDF), is a kind of glycoprotein with a molecular weight of 44 KD. As the ligand of tyrosine kinase receptor of ErbB family, neuregulin is responsible for cell signaling. NRG family has four members: NRG1, NRG2, NRG3 and NRG4 (Falls et al., Exp Cell Res. 284:14-30,2003). NRG1 plays an important role in nervous system, heart and breast. It is also evidenced that NRG1 signal transmission plays a part in the development and function of other organ systems, as well as in the pathogenesis of human diseases (including schizophrenia and breast cancer). NRG1 has many isomers. The research in gene mutated mice (gene knock-out mice) indicates that isomers with different N terminal region or EGF-like domain have different in vivo functions. The present invention is based on NRG-1β.

NRG-1β is a transmembrane protein (Holmes et al., Science 256, 1205-1210,1992). The extracellular region is N terminal region, comprising immune globulin like domain (Ig-like domain) and EGF-like domain. The intracellular region is C terminal region. Under the action of extracellular matrix metalloproteinase, the extracellular region of NRG is in a free state after being cut off by enzyme, thus facilitate binding to ErbB3 receptor on the cell surface and activating relevant cell signal transmission.

EGF receptor family can be divided into four classes, including ErbB1, ErbB2, ErbB3 and ErbB4, all of which are transmembrane proteins with a molecular weight of around 180-185 KD. They all comprise an extracellular ligand-binding domain in N terminal region except ErbB2. They all have protein tyrosine kinase activity in intracellular C terminal region except ErbB3. ErbB1 is epidermal growth factor receptor while ErbB3 and ErbB4 are neuregulin receptors. Among these neuregulin receptors, only ErbB2 and ErbB4 are highly expressed in heart (Yarden et al., Nat Rev Mol Cell Biol, 2: 127-137,2001).

After NRG binds to the extracellular domain of ErbB3 or ErbB4, it induces the formation of heterodimers of ErbB3, ErbB4 with other ErbB receptors (normally including ErbB2) or homodimer of ErbB4, which results in phosphorylation of the receptor's intracellular region (Yarden et al., Nat Rev Mol Cell Biol, 2: 127-137,2001). The phosphorylated intracellular domain then binds signaling proteins inside the cell, thus activating the downstream AKT or ERK signaling pathway, and inducing a series of cell reactions, such as stimulation or depression of cell proliferation, cell apoptosis, cell migration, cell differentiation or cell adhesion.

NRG plays an particularly important role in the development of heart (WO0037095, CN1276381, WO03099300, WO9426298, U.S. Pat. No. 6,444,644, WO9918976, WO0064400, Zhao et al., J. Biol. Chem. 273, 10261-10269, 1998). At the early stage of embryo development, the expression of NRG is limited in endocardium, whereafter it is released to periphery myocardial cell by paracrine and binds to the extracellular domain of protein tyrosine kinase receptors ErbB4 on cytomembrane, the ErbB4 than forms a heterodimer with ErbB2. The formation and activation of the ErbB4/ErbB2 complex is essential to form the trabecular of sponge-like heart at early phase. The absence of any of the three protein genes for NRG proteins, ErbB4 and ErbB2, would lead to an embryo without trabecular and death in uterus at early development. WO0037095 shows that a certain concentration of neuregulin could sustainably activate ERK signaling pathway, promote the differentiation and growth of myocardial cells, guide the reconstruction of sarcomere and cytoskeleton at the site where myocardial cells are adhered to cells, improve the structure of myocardial cells and enhance myocardial cell contraction. WO0037095 and WO003099300 also indicate that NRG could be used in the detection, diagnosis and treatment of various cardiovascular diseases.

The following is a list of some prior art technical literature related to the present invention: 1. Cardiac muscle function and manipulation:WO0037095; 2. New application of neuregulin and its analogs: CN1276381; 3. Neuregulin based methods and composition for treating cardiovascular diseases: WO03099300; 4. Zhao Y Y, Sawyer D R, Baliga R R, Opel D J, Han X, Marchionni M A and Kelly R A. Neuregulins PromoteSurvival and Growth of Cardiac Myocytes. J. Biol. Chem. 273, 10261-10269 (1998); 5. Methods for treating muscle diseases and disorder: WO9426298; 6. Methods of increasing myotube formation or survival or muscle cell mitogenesis, differentiation or survival using a neuregulin: U.S. Pat. No. 6,444,642. 7. Therapeutic methods comprising use of a neuregulin: WO9918976; 8. Methods for treating congestive heart failure: WO0064400; 9. Holmes W E, Sliwkowski M X, Akita R W, Henzel W J, Lee J, Park J W, Yansura D, Abadi N, Raab H, Lewis G D, et al. Identification of heregulin, a specific activator p185erbB2. Science 256, 1205-1210 (1992); 10. Falls D L. Neuregulins: functions, forms and signaling strategies. Experimental Cell Research, 284, 14-30 (2003). 11. Yarden Y, Sliwkowski X. Untangling the ErbB signaling Network. Nature Reviews: Molecular Cell Biology, 2127-137 (2001).

Arrhythmia is due to abnormal excitement of sinoatrial node or excitement out of the sinoatrial node, slow conduction, conduction block or conduction by abnormal channel, namely origin and (or) conduction disorders of heart activity leads to abnormal heart beat frequency and (or) allorhythmia. According to the site of origin, arrhythmia can be divided into sinus arrhythmia, atrial arrhythmia, arrhythmia originated from atrioventricular junction and ventricular arrhythmia. Among them, ventricular arrhythmia is the most common one. Ventricular arrhythmia refers to cardiac arrhythmia originated from ventricule, and includes ventricular premature beat (VPB), ventricular tachycardia (VT) and ventricular fibrillation (VF) etc.

Arrhythmia can be found in a variety of organic heart diseases, more commonly incoronary heart disease (CHD), cardiomyopathy, myocarditis and rheumatic heart disease (RHD), especially in the occurrence of heart failure or acute myocardial infarction. Arrhythmias in generally healthy people, or in patients with autonomic nervous dysfunction are not uncommon. There are other causes such as electrolyte or endocrine disorders, anesthesia, hypothermia, thoracic or cardiac surgery, drug action and diseases of the central nervous system, part with unknown etiology.

Nearly 50 antiarrhythmic drugs have been put into clinical use. So far there is still no unified classification standard. According to the different action mechanism, antiarrhythmic drugs are classified into the following four categories. In order to guide the clinical rational use of drugs, class I drugs are further classified into subtypes A, B and C.
(1) Class I drugs—sodium channel blockers
   1) Class I A drugs moderate sodium channel blockade, such as quinindium etc.
   2) Class I B drugs mild sodium channels blockade, such as lidocaine etc.
   3) Class I C drugs obvious sodium channel blockade, such as flecainide etc.
(2) Class II drugs—β adrenergic receptor blockers
The effect is due to blocking β receptors, and the representative drug is propranolol.
(3) Class III drugs—the drugs prolonging the process of repolarization
This category of drugs includes amiodarone.
(4) Class IV drugs—calcium antagonists
They block the calcium channel and inhibit the internal flow of Ca, and the representative drug is verapamil.

Long term use of antiarrhythmic drugs have different degrees of side effects, thereinto serious side effects are fatal by causing heart block. Ventricular arrhythmia has a high incidence rate, severe prognosis and high risk of long-term drug therapy, the treatment of moderate ventricular arrhythmia, severe ventricular arrhythmia or ventricular arrhythmia accompanied with congestive heart failure (CHF) is very difficult, and many antiarrhythmic drugs cannot be used.

So far, no prior art technical literature has disclosed regulation of ventricular arrhythmia by neuregulin, or effect of neuregulin on ventricular premature beat (VPB), ventricular tachycardia (VT) and ventricular fibrillation (VF) etc.

The present invention found that mammalian neuregulin proteins can greatly reduce or delay the incidence of ventricular arrhythmias and/or ventricular premature beat in patients with heart failure, and may significantly shorten the QTc interval.

THE CONTENT OF THE INVENTION

A. Summary of the Invention
The present invention is based on the scientific discovery that NRG is crucial to the heart development, as well as maintenance of function of adult heart. The present invention is also based on the scientific discovery that NRG can strengthen the sarcomere and cytoskeleton of myocardial cells, and the formation of intercellular junction. The present invention is further based on the scientific discovery that NRG can improve the heart function of animals or patients with heart failure in animal models and clinical trials. Neuregulin, neuregulin polypeptide, neuregulin derivatives, or compounds which mimic the activities of neuregulins all fall within the scope of the present invention.

The NRG proteins can bind to the ErbB receptor on the surface of myocardial cells, continuously activate the ERK signal pathway in the cell, and change the structure of the myocardial cells, thereby enhance myocardial contractility, so it is used for the treatment of heart failure. After administration of NRG in patients with heart failure, the results showed that the NRG protein could change the human heart rhythm and shorten the QTc interval. In particular, NRG can greatly reduce the incidence of ventricular arrhythmias and/or ventricular premature beat.

In a first aspect of the present invention, a method is provided for preventing, treating or delaying ventricular arrhythmias and/or ventricular premature beat in mammals especially human, including administering an effective amount of NRG or its functional fragment, or nucleic acid encoding NRG or its functional fragment, or substance improving the yield of NRG and/or functional to mammals especially human who need or hope to prevent, treat or delay ventricular arrhythmias and/or ventricular premature beat, so as to achieve the effect in preventing, treating or delaying ventricular arrhythmias and/or ventricular premature beat.

In a second aspect, the present invention provides a pharmaceutical preparation for preventing, treating or delaying ventricular arrhythmias and/or ventricular premature beat in mammals especially human, which comprises an effective amount of NRG or its functional fragment, or nucleic acid encoding NRG or its functional fragment, or substance improving the yield of NRG and/or functional, and pharmaceutically acceptable carriers, excipients etc. The pharmaceutical preparation can be used in combination with other drug(s) for preventing, treating or delaying ventricular arrhythmias and/or ventricular premature beat.

In another aspect, the present invention provides a composition for preventing, treating or delaying ventricular arrhythmias and/or ventricular premature beat in mammals especially human, which comprises the pharmaceutical preparation for preventing, treating or delaying ventricular arrhythmias and/or ventricular premature beat in mammals provided by this invention, and other drug(s) for preventing, treating or delaying ventricular arrhythmias and/or ventricular premature beat.

In a further aspect, the present invention provides a kit for preventing, treating or delaying ventricular arrhythmias and/or ventricular premature beat in mammals especially human, which comprises one or more doses of said pharmaceutical preparation or composition for preventing, treating or delaying ventricular arrhythmias and/or ventricular premature, and instructions on how to use the pharmaceutical preparation or composition.

The pharmaceutical preparation or composition provided by the invention can be administered before, after or at the time of the occurrence of the ventricular arrhythmias and/or ventricular premature beat.

B. Definitions
Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" refers to proteins or peptides that can bind and activate ErbB2, ErbB3, ErbB4 or heterodimers or homodimers thereof, including neuregulin isoforms, neuregulin EGF-like domain, polypeptides comprising neuregulin EGF-like domain, neuregulin mutants or derivatives, and any kind of neuregulin-like gene products that can activate the above receptors. Neuregulin also includes NRG-1, NRG-2, NRG-3 and NRG-4 proteins, peptides, fragments and compounds that have the functions of neuregulin. In preferred embodiments, neuregulin is a protein or peptide that can bind to and activate ErbB2/ErbB4 or ErbB2/ErbB3 heterodimers, for example, but not for the purpose of restriction, peptides of the present invention include a fragment of the NRG-1 β2 isoform, i.e., the 177-237 amino acid fragment, which contains the EGF-like domain having the following amino acid sequence: SHLVK-CAEKEKTFCVNGGECFMVKDLSNPSRYLCKCPNEFT-GDRCQNYVMASFYKAEELYQ (SEQ ID NO: 2). The NRG proteins of the present invention can activate the receptors above and regulate their biological functions, for example, stimulate the synthesis of acetylcholine receptors in skeletal muscle cells, promote the differentiation and survival of cardiomyocytes and DNA synthesis. The NRG proteins also comprise NRG mutants that possess conservative mutation having no substantially affect on biological function. It is well known to those of skill in this art that mutation of single amino acid in non-critical region generally would not alter the biological activity of the resulting protein or polypepdite (see, e.g., Watson et al., Molecular Biology of the Gene, 4th Edition, 1987, The Bejacmin/Cummings Pub.co., p.224). The NRG proteins of the invention can be isolated from natural sources, or obtained through recombination technology, artificial synthesis or other means.

As used herein, "epidermal growth factor-like domain" or "EGF-like domain" refers to a polypeptide fragment encoded by the neuregulin gene that binds to and activates ErbB2, ErbB3, ErbB4, or heterodimers or homodimers thereof, and structurally similar to the EGF receptor-binding domain as disclosed in WO 00/64400, Holmes et al., Science, 256:1205-1210(1992); U.S. Pat. Nos. 5,530,109 and 5,716,930; Hijazi et al., Int. J. Oncol., 13:1061-1067 (1998); Chang et al., Nature, 387:509-512(1997); Carraway et al., Nature, 387:512-516(1997); Higashiyama et al., J. Biochem., 122:675-680(1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain refers to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO:3), as described in U.S. Pat. No. 5,834,229.

As used herein, "arrhythmia" refers to abnormal excitement of sinoatrial node or excitement out of the sinoatrial node, slow conduction, conduction block or conduction by abnormal channel, namely origin and (or) conduction disorders of heart activity leads to abnormal heart beat frequency and (or) allorhythmia. Arrhythmia is an important disease in cardiovascular diseases. It can occur separately or accompany with cardiovascular disease. It may occur suddenly and lead to sudden death, or continuously affect the heart and lead to heart failure. According to the site of origin, arrhythmia can be classified into sinus arrhythmia, atrial arrhythmia, arrhythmia originated from atrioventricular junction and ventricular arrhythmia.

As used herein, "ventricular arrhythmia" refers to ventricular arrhythmia originated from ventricule, particularly refers to ventricular premature beat (VPB), ventricular tachycardia (VT), ventricular fibrillation (VF) an so on. Ventricular premature beat comprises bigeminy, trigeminy, ventricular parasystole. Ventricular tachycardia comprises paroxysmal ventricular tachycardia, accelerated idioventricular rhythm, torsade de points type of ventricular tachycardia. The number of ventricular premature beat increases with age, but the number of complicated ventricular premature beat is not increased. The abnormal ECG detection rate of the elderly with higher level of ventricular premature beat (Lown classification) is higher, often accompanied by myocardial hypertrophy, myocardial infarction and other abnormal performance. VPB may have different clinical significance and prognosis under different situations, and is associated with the presence or absence of organic heart disease, types of heart disease and condition of heart function. Ventricular tachycardia is short for VT, and is common in AMI, ventricular aneurysm, heart failure, electrolyte disorder and drug poisoning etc. TDP is due to multiple circuit reentry or irregular reentry caused by increased dispersion of ventricular repolarization. It is common in low potassium, intoxication of quinidine, amiodarone, tricyclic antidepressant. Ventricular flutter and ventricular fibrillation is common in ischemic heart disease. In addition, anti arrhythmia drugs, in particular the drugs that may cause QT interval prolongation and torsade de points, severe hypoxia, ischemia, pre-excitation syndrome with atrial fibrillation and fast ventricular rate, electrical injury may also cause it.

As used herein, "QTc interval" refers to QT interval adjusted according to the heart rate, which is an indicator of cardiac depolarization and repolarization. QTc prolongation indicates the delay of cardiac repolarization, reflects the abnormal ECG, and usually closely relates to increased arrhythmia susceptibility. Under the normal range, i.e., male<430 ms, female<450 ms, the incidence of QTc prolongation is not high, but potentially hazardous, mostly shows significant torsades de pointes tachycardia, and can induce ventricular arrhythmias and even sudden death in severe cases.

As used herein, "other anti arrhythmia drugs" refers to drug known to be used for treatment of arrhythmias, including sodium channel blockers, such as moderate sodium channels blocker quinindium, mild sodium channel blocker lidocaine, significant sodium channel blocker flecainide; beta adrenergic receptor blockers, such as propranolol;

drugs prolonging the repolarization process selectively, such as amiodarone, and calcium antagonists, etc.

Figure 1:
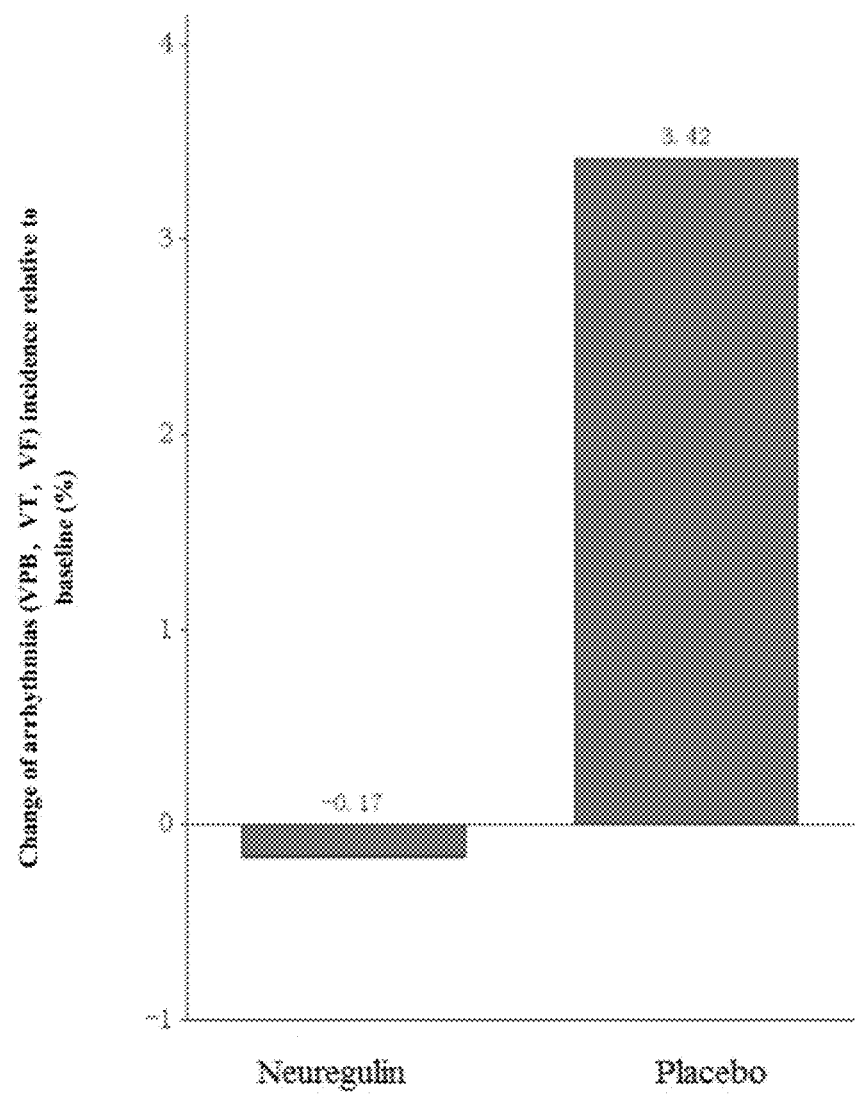
FIG. 1: Comparison of change of ventricular arrhythmias (VPB, VT, VF) incidence before administration relative to baseline between the two groups (p<0.001).

The invention will be further illustrated by reference to the following examples. It should be understood that the examples are illustrative, but not limiting.

EXAMPLES

Example 1

A Randomized, Double-Blinded, Multi-Center, Placebo Controlled, Standard Treatment Based Study to Evaluate the Effect of Recombinant Human Neuregulin on the Survival of Patients with Chronic Heart Failure To evaluate the efficacy of recombinant human neuregulin-1 for injection on chronic heart failure, a phase II, double-blinded, multi-center, placebo controlled, standard treatment based study was carried out in multiple clinical centers in China. A total of 351 patients with NYHA Class III or IV stable chronic heart failure were enrolled and randomized into two groups: placebo, or 0.6 μg/kg rhNRG-1. There were no significant variations in demographics or background therapies between the two groups. According to the schedule, patients were administered the drug for 10 consecutive days in the hospital first, and were allowed to be discharged from the hospital on the 11$^{th}$ day. Then they were administered the drug once a week as outpatient from the 3$^{rd}$ week to the 25$^{th}$ week. Survival information was collected during the fifty-third week of the study. The 12 lead ECG was examined before and after each administration.

Investigational drug:

Specification: Neucardin™, the EGF-like domain of Neuregulin-1 β2 isoform is constituted of 61 amino acids, with the molecular weight of 7054 Dal (1 μg=0.14 nmol). 250 μg (5000 EU)/vial (1 μg=20 EU).

Placebo

Specification: excipients of Neucardin™ (250 μg/vial, without the active ingredient of recombinant human NRG-1 protein)

Dosage form: Powder injection.

Storage: in safe place, kept away from light, at 3-8° C.

Mode of administration: Intravenously drip or infusion.

Dosing regimen:

|  | 1-10 day | 3-25 weeks |
| --- | --- | --- |
| Dosage | 0.6 μg/kg/day rhNRG-1 or placebo | 0.8 μg/kg/day rhNRG-1 or placebo |
| Administration route | Intravenously drip | Intravenously infusion |
| regimen | 10 hours per day, for consecutive 10 days | 10 minutes infusion each week |

The clinical inclusion criteria: chronic heart failure patients with a NYHA classification of III or IV at the age of 18-65 were considered for enrollment if they had left ventricular ejection fraction (LVEF) of ≤40%, and stable clinical symptoms(including clinical symptoms, signs and standard therapy for heart failure has reached the target dose or maximum tolerated dose for more than 1 months).

Major exclusion criteria includes acute myocardial infarction, hypertrophic cardiomyopathy, constrictive pericarditis, significant valve disease or congenital heart disease, severe pulmonary hypertension, systolic blood pressure <90 mmHg or >160 mmHg, severe ventricular arrhythmia, cardiac surgery or a cerebrovascular event within the previous six months, claustrophobia or pregnant female subjects.

All patients provided written consent.

The study included three stages, namely, the screening period, the administration period and the follow-up period after drug withdrawal. The whole study period was 12 months (52 weeks). A total of 35 on-site visits and 2 telephone interviews was proceeded, and a number of indicators was observed during the study process (see Table 1).

TABLE 1

| Study process and observational indicators | | | | | | | | | | | | | | |
| --- | --- | --- | --- | --- | --- | --- | --- | --- | --- | --- | --- | --- | --- | --- |
| Study Cycle | screening and baseline | 1 week | | | | | | | 2 weeks | | | 3 weeks | 4 weeks |
| Visit Frequency | 1 | 2 | 3 | 4 | 5 | 6 | 7 | 8 | 9 | 10 | 11 | 12 | 13 |
| Administration Frequency | | 1 | 2 | 3 | 4 | 5 | 6 | 7 | 8 | 9 | 10 | 11 | 12 |
| Inclusion/Exclusion Criteria | X | | | | | | | | | | | | |
| Clinical History | X | | | | | | | | | | | | |
| Weight | X | | | | | | | | | | | | |
| Vital Signs | X | X | X | X | X | X | X | X | X | X | X | X | X |
| Drug Combination | X | X | X | X | X | X | X | X | X | X | X | X | X |
| Two Dimensional Echocardiogram | X | | | | | | | | | | | | |
| Heart Function Grade of NYHA | X | | | | | | | | | | | | X |
| Urine Pregnancy Test (Childbearing Age) | X | | | | | | | | | | | | X |
| Routine Blood, Urine Test, Blood Biochemistry, CTnT | X | | | | | | | | | | | | X |

TABLE 1-continued

Study process and observational indicators

| | | | | | | | | | | | | | |
|---|---|---|---|---|---|---|---|---|---|---|---|---|---|
| Coagulation Function Test (APTT, PT) | X | | | | | | | | | | | | X |
| 12 Lead ECG | X | X | X | X | X | X | X | X | X | X | X | X | X |
| 6-min walk test | X | | | | | | | | | | | | X |
| NT-proBNP | X | | | | | | | | | | | | X |
| Anti-rhNRG-1β2 | X | | | | | | | | | | X | | X |
| Chest Radiography | X | | | | | | | | | | | | |
| Organization B ultrasonic (mammary gland, liver and gall, spleen, pancreas, kidney, adrenal gland, pelvic cavity) | X | | | | | | | | | | | | |
| Urine Volume for 24 hours | X | X | X | X | X | X | X | X | X | X | X | | |
| Administration of Study Drugs | | X | X | X | X | X | X | X | X | X | X | X | X |
| Dyspnea Assessment | X | | | | | | | | | | | | X |
| Life Quality Evaluation | X | | | | | | | | | | | | X |
| Adverse Event/Serious Adverse Event | X | X | X | X | X | X | X | X | X | X | X | X | X |
| Telephone Visits | | | | | | | | | | | | | |

| | | | | follow-up period | | | |
|---|---|---|---|---|---|---|---|
| Study Cycle | 5-11 weeks | 12 weeks | 13-24 weeks | 25 weeks | 35 weeks | 45 weeks | 52 weeks |
| Visit Frequency | 14-20 | 21 | 22-33 | 34 | | | 35 |
| Administration Frequency | 13-19 | 20 | 21-32 | 33 | | | |
| Inclusion/Exclusion Criteria | | | | | | | |
| Clinical History | | | | | | | |
| Weight | | X | | X | | | X |
| Vital Signs | X | X | X | X | | | X |
| Drug Combination | X | X | X | X | | | X |
| Two Dimensional Echocardiogram | | X | | X | | | X |
| Heart Function Grade of NYHA | | X | | X | | | X |
| Urine Pregnancy Test (Childbearing Age) | | X | | X | | | X |
| Routine Blood, Urine Test, Blood Biochemistry, CTnT | | X | | X | | | X |
| Coagulation Function Test (APTT, PT) | | X | | X | | | X |
| 12 Lead ECG | X | X | X | X | | | X |
| 6-min walk test | | X | | X | | | X |
| NT-proBNP | | X | | X | | | X |
| Anti-rhNRG-1β2 | | X | | X | | | X |
| Chest Radiography | | | | | | | X |
| Organization B ultrasonic (mammary gland, liver and gall, spleen, pancreas, kidney, adrenal gland, pelvic cavity) | | | | | | | |
| Urine Volume for 24 hours | | | | | | | |
| Administration of Study Drugs | X | X | X | X | | | |
| Dyspnea Assessment | | X | | X | | | X |
| Life Quality Evaluation | | X | | X | | | X |
| Adverse Event/Serious Adverse Event | X | X | X | X | X | X | X |
| Telephone Visits | | | | | X | X | |

Figure 4:
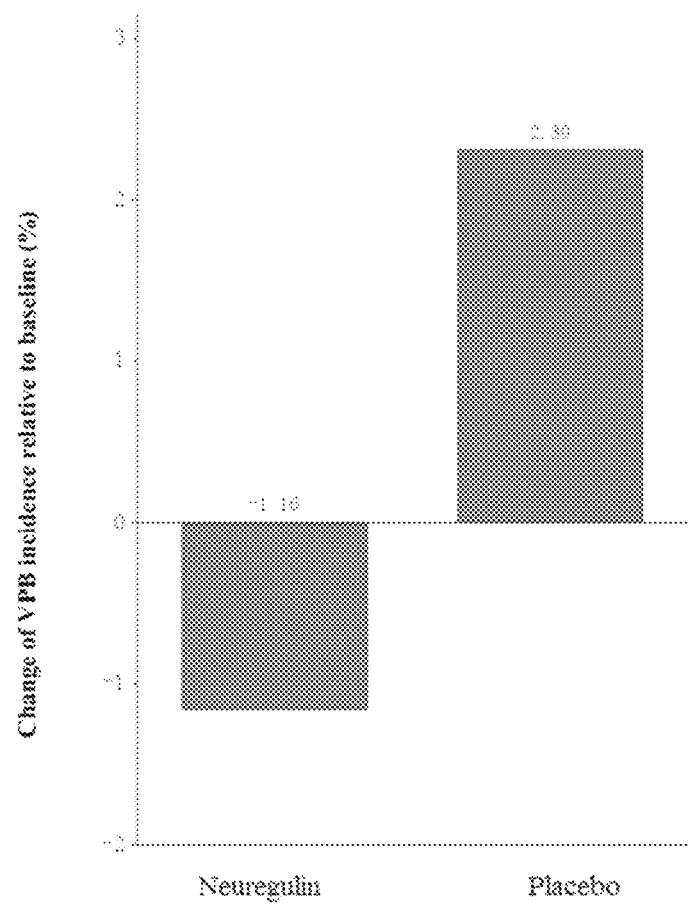
FIG. 4: Comparison of change of VPB incidence before administration relative to baseline between the two groups.
Figure 5:
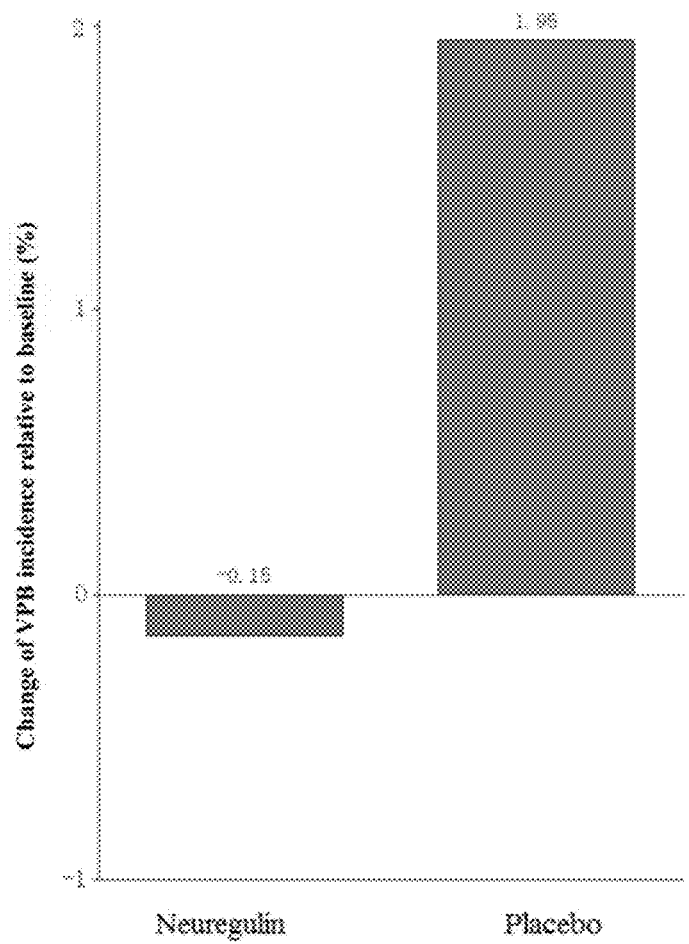
FIG. 5: Comparison of change of VPB incidence after administration relative to baseline between the two groups
Figure 6:
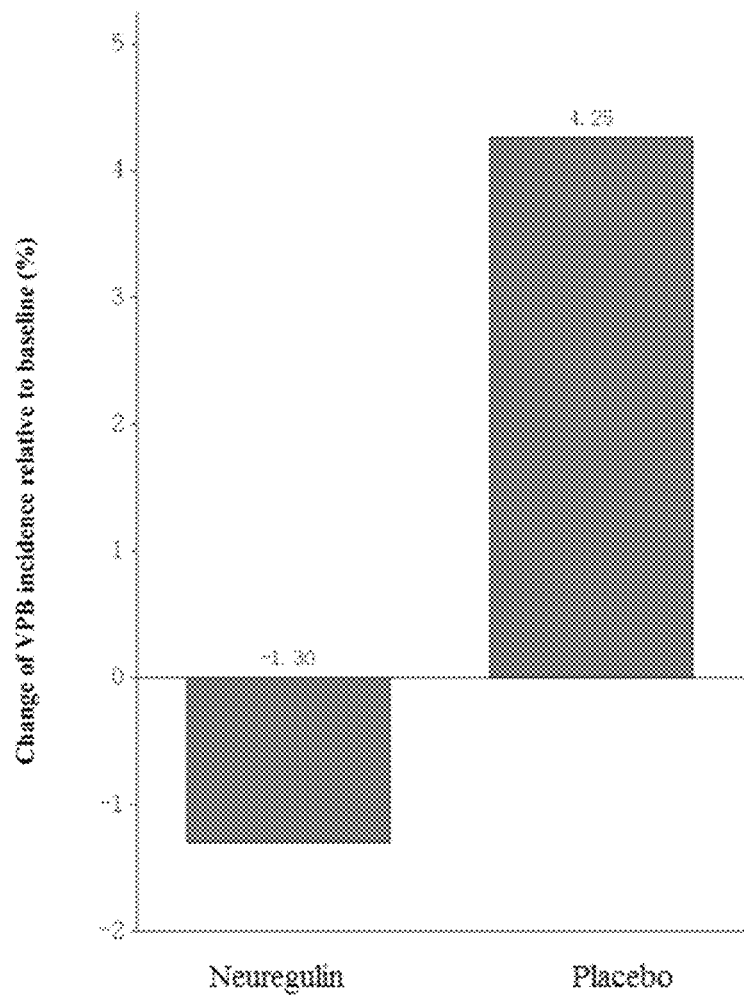
FIG. 6: Comparison of change of the sum of VPB incidence before/after administration relative to baseline between the two groups

Results and data analysis:

This study analyzed all ECG, described the abnormal change of ECG before and after each administration, analyzed the parameters changes of ECG before and after each administration, including heart rate, QRS interval, PR interval, RR interval, QT interval, QTc. The central tendency (mean, standard deviation, median) and classification analysis of QTc was carried out. Rank sum test was used in group comparison, and WILCOXON rank sum test was used for comparison between groups. Table 2 shows baseline of ECG diagnosis and parameters of all selected patients. The comparison of change of ventricular arrhythmias (VPB, VT, VF) incidence before each administration relative to baseline between the two groups was shown in Table 3 and FIG. 1. The comparison of change of ventricular arrhythmias (VPB, VT, VF) incidence after each administration relative to baseline between the two groups was shown in Table 4 and FIG. 2. The comparison of change of ventricular arrhythmias (VPB, VT, VF) incidence before/after each administration relative to baseline between the two groups was shown in Table 5 and FIG. 3. In addition, the VPB was further analyzed. The comparison of change of VPB incidence before each administration relative to baseline between the two groups was shown in Table 6 and FIG. 4. The comparison of VPB incidence change after each administration relative to baseline between the two groups was shown in Table 7 and FIG. 5. The comparison of VPB incidence change before/after each administration relative to baseline between the two groups was shown in Table 8 and FIG. 6. In addition, the frequency distribution analysis of QTc change of all patients after each administration was shown in FIG. 7.

TABLE 2

Comparison of ECG diagnosis and parameter between two groups of subjects at baseline

| | | Neucardin™ Group | Placebo Group | Between groups |
|---|---|---|---|---|
| ECG Diagnosis | Normal ECG | 5 (3.01%) | 3 (1.80%) | 0.340 |
| | Abnormal/NCS | 16 (9.64%) | 24 (14.37%) | |

TABLE 2-continued

Comparison of ECG diagnosis and parameter between two groups of subjects at baseline

| | | Neucardin ™ Group | Placebo Group | Between groups |
|---|---|---|---|---|
| | Abnormal/CS | 145 (87.35%) | 140 (83.83%) | |
| Cardiac Rhythm | Sinus rhythm | 128 (77.1) | 129 (77.2) | 0.976 |
| | Arrhythmia | 38 (22.9) | 38 (22.8) | |
| | VPB | 19 (11.4%) | 10 (6.0%) | 0.077 |
| | VT | 1 (0.6) | 0 (0%) | 0.498 |
| | VF | 0 (0%) | 0 (0%) | |
| Heart rate | | 77.2 ± 17.0 (n = 166) | 79.1 ± 16.1 (n = 167) | 0.2909 |
| RR interval (ms) | | 829.16 ± 182.21 (n = 145) | 782.60 ± 168.90 (n = 146) | 0.0245 |
| QT interval (ms) | | 405.05 ± 53.14 (n = 166) | 392.08 ± 45.16 (n = 167) | 0.0169 |
| QTc (ms) | | 445.68 ± 45.45 (n = 165) | 433.61 ± 39.95 (n = 164) | 0.011 |

Note:
NCS means non-clinical significance;
CS means clinical significance

As shown in Table 2, the rate of abnormal ECGs (87.35% vs 83.83%) and rate of arrhythmias (22.9% vs 22.8%) between Neucardin™ and placebo group were comparable at baseline (p>0.05), however, RR interval (829.2±182.2 ms vs 782.6±168.9 ms) and QTc interval (445.7±45.5 ms vs 433.6±39.9 ms) were significantly longer for Neucardin™ group compared to placebo group (p=0.0245 and 0.011 respectively).

TABLE 3

The comparison of change of ventricular arrhythmia (ventricular premature beat, ventricular tachycardia, and ventricular fibrillation) incidence before administration relative to baseline in two groups of subjects ($p < 0.0001$)

| | Neucardin ™ Group (N = 175) | Placebo Group (N = 176) | P value |
|---|---|---|---|
| N | 34 | 34 | <.0001 |
| Mean (SD) | −0.168 (3.301) | 3.417 (3.450) | |
| Median | −0.333 | 3.175 | |
| Min, Max | −7.16, 6.48 | −2.42, 9.76 | |

Table 3 shows the difference value between the incidence of ventricular arrhythmia before administration and the incidence of ventricular arrhythmia at baseline. N is the times of ECG diagnosis. Mean is mean value. Median is medium value. Min and Max are the minimum value and maximum value in these difference value, respectively.

TABLE 4

The comparison of ventricular arrhythmia (ventricular premature beat, ventricular tachycardia, and ventricular fibrillation) incidence after administration relative to baseline in two groups of subjects ($p < 0.0001$)

| | Neucardin ™ Group (N = 175) | Placebo Group (N = 176) | P value |
|---|---|---|---|
| N | 34 | 34 | 0.1570 |
| Mean (SD) | 1.414 (3.764) | 2.700 (3.640) | |
| Median | 1.863 | 2.377 | |
| Min, Max | −5.79, 7.67 | −4.56, 11.39 | |

Table 4 shows the difference value between the incidence of ventricular arrhythmia after administration and the incidence of ventricular arrhythmia at baseline. N is the times of ECG diagnosis. Mean is mean value. Median is medium value. Min and Max are the minimum value and maximum value in these difference value, respectively.

TABLE 5

The comparison of the sum of ventricular arrhythmia (ventricular premature beat, ventricular tachycardia, and ventricular fibrillation) incidence before and after administration relative to baseline in two groups of subjects ($p < 0.0001$)

| | Neucardin ™ Group (N = 175) | Placebo Group (N = 176) | P value |
|---|---|---|---|
| N | 34 | 34 | 0.0007 |
| Mean (SD) | 1.246 (5.656) | 6.117 (5.614) | |
| Median | 1.368 | 5.265 | |
| Min, Max | −10.88, 13.14 | −5.66, 20.27 | |

Table 5 shows the difference value between the sum of incidence of ventricular arrhythmia (ventricular premature beat, ventricular tachycardia, and ventricular fibrillation) in two groups of subjects before and after administration and the incidence of ventricular arrhythmia of baseline. N is the times of ECG diagnosis. Mean is mean value. Median is medium value. Min and Max are the minimum value and maximum value in these difference value, respectively.

TABLE 6

The comparison of change of VPB incidence before administration relative to baseline in two groups of subjects ($p < 0.0001$)

| | Neucardin ™ Group (N = 175) | Placebo Group (N = 176) | P value |
|---|---|---|---|
| N | 34 | 34 | <0.0001 |
| Mean (SD) | −1.158 (1.793) | 2.303 (2.005) | |
| Median | −1.100 | 1.800 | |
| Min, Max | −4.60, 2.60 | −1.90, 6.80 | |

Table 6 shows the difference value between incidence of VPB in two groups of subjects before administration and incidence of VPB at the baseline. N is the times of ECG diagnosis. Mean is mean value. Median is medium value. Min and Max are the minimum value and maximum value in these difference value, respectively.

TABLE 7

The comparison of change of VPB incidence after administration relative to baseline in two groups of subjects (p < 0.0001)

|  | Neucardin ™ Group (N = 175) | Placebo Group (N = 176) | P value |
|---|---|---|---|
| N | 34 | 34 | <0.001 |
| Mean (SD) | −0.145 (2.198) | 1.952 (2.140) |  |
| Median | −0.400 | 1.600 |  |
| Min, Max | −4.40, 4.50 | −1.70, 8.10 |  |

Table 7 shows the difference value between incidence of VPB in two groups of subjects after administration and baseline. N is the times of ECG diagnosis. Mean is mean value. Median is medium value. Min and Max are the minimum value and maximum value in these difference value, respectively.

TABLE 8

The comparison of the sum of VPB incidence before and after administration relative to baseline in two groups of subjects (p < 0.0001)

|  | Neucardin ™ Group (N = 175) | Placebo Group (N = 176) | P value |
|---|---|---|---|
| N | 34 | 34 | <0.0001 |
| Mean (SD) | −1.303 (3.079) | 4.255 (3.485) |  |
| Median | −1.500 | 3.700 |  |
| Min, Max | −7.80, 5.30 | −0.80, 14.90 |  |

Table 8 shows the difference value between the sum of incidence of VPB in two groups of subjects before and after administration and incidence of VPB at baseline. N is the times of ECG diagnosis. Mean is mean value. Median is medium value. Min and Max are the minimum value and maximum value in these difference value, respectively.

Conclusions:

The incidence of arrhythmias at baseline were 22.9% and 22.8% in the Neucardin™ and placebo group respectively, including VPB incidence of 11.4% and 6.0%, VT incidence of 0.6% and 0%, VF incidence of 0% and 0% in the Neucardin™ group and placebo group, respectively. There were no significant differences for VPB, VT and VF incidence between the two groups.(see Table 2)

Figure 2:
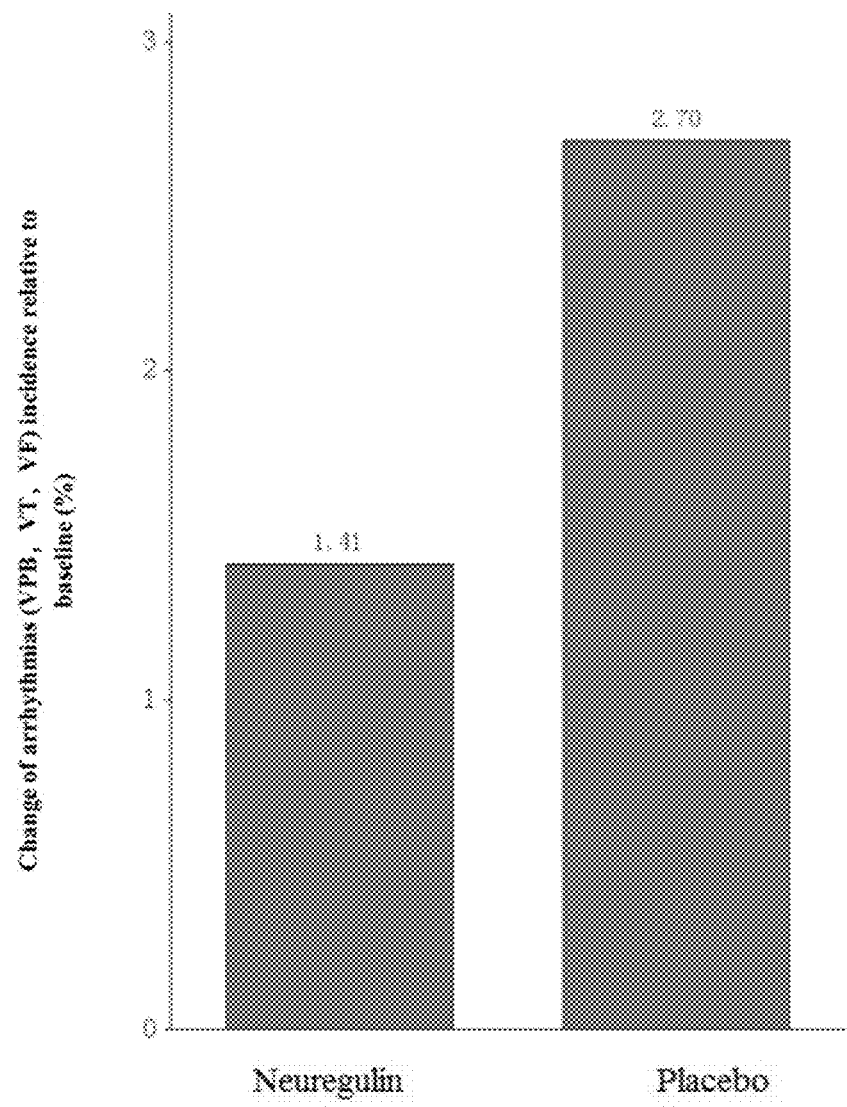
FIG. 2: Comparison of change of ventricular arrhythmias (VPB, VT, VF) incidence after administration relative to baseline between the two groups.
Figure 3:
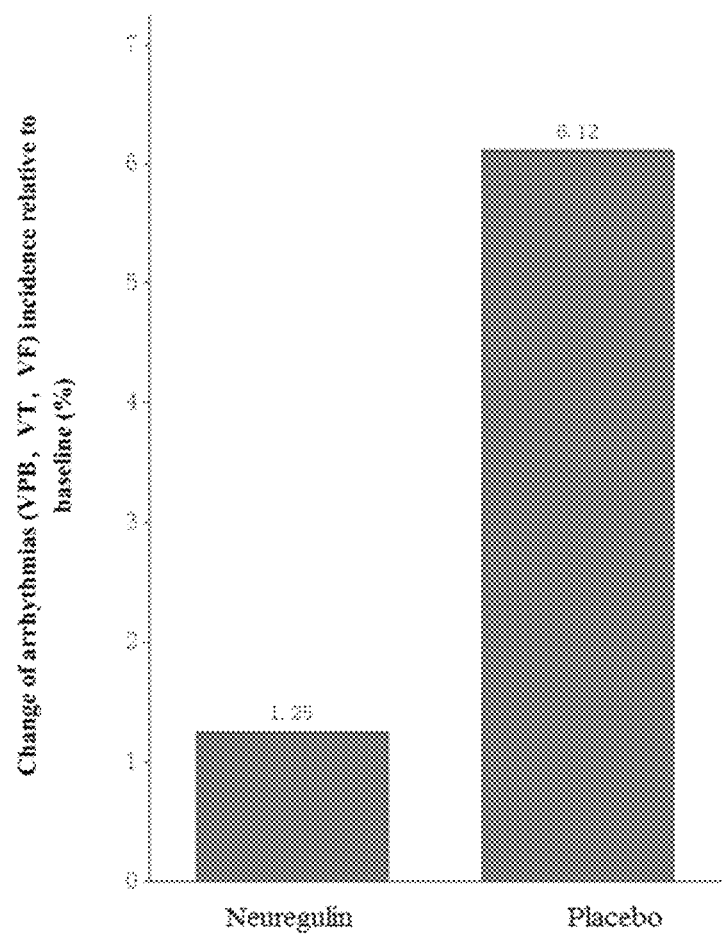
FIG. 3: Comparison of change of the sum of ventricular arrhythmias (VPB, VT, VF) incidence before/after administration relative to baseline between the two groups.

The data shown in Tables 3, 4, and 5 indicate that among the ECG tests throughout the study (before/after study drug administrations, 68 times in total), there was a very significant decreasing trend of incidence of ventricular arrhythmias in the Neucardin™ group compared with the placebo group before and after administration (p<0.0001).The results were shown in FIGS. 1, 2, and 3.

In addition, the ventricular premature beat was further analyzed. The change of incidence of premature ventricular beat before/after administration relative to baseline, as shown in table 6, 7 and 8, indicated that there is a very significant decreasing trend of the incidence of ventricular premature beat in the Neucardin™ group compared with the placebo group (p<0.0001). The results were shown in FIGS. 4, 5, and 6.

Figure 7:
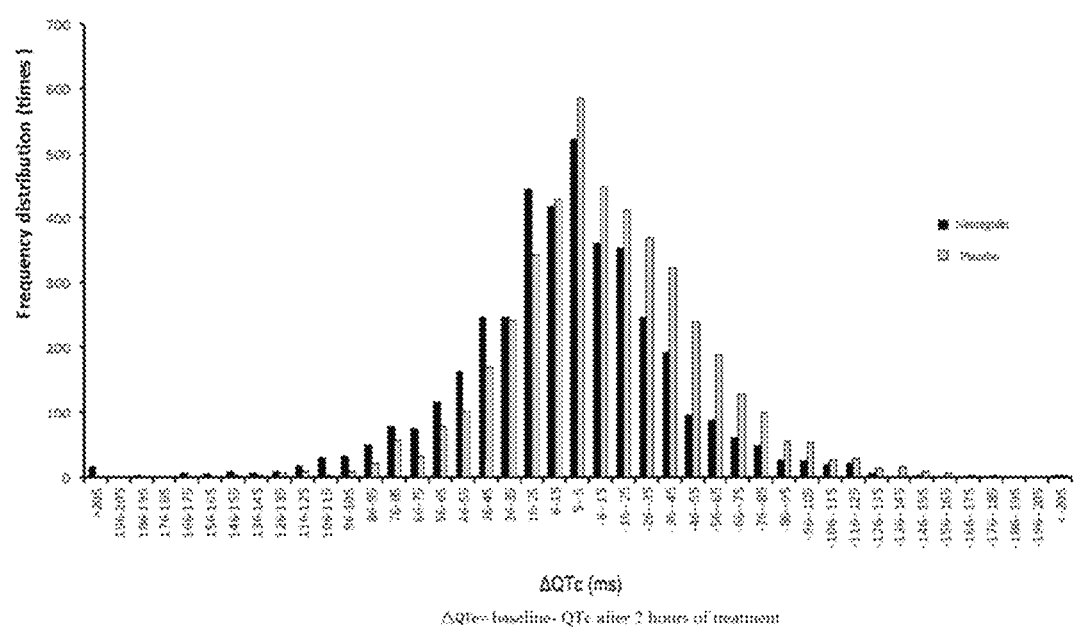
FIG. 7: Frequency distribution of QTc changes after each administration relative to baseline baseline to the subject.

Although the RR interval, QT interval and QTc interval were longer in Neucardin™ group than in the placebo group at baseline, the QTc intervals were not progressively prolonged after Neucardin™ administration compared to baseline, instead, the majority showed a tendency of significant shortening. Analysis of the QTc change frequency distribution after Neucardin™ administration indicated that the QTc intervals of Neucardin™ group generally showed a shortening trend compared with placebo group (FIG. 7).

Comprehensive analysis of the ECG diagnostics and parameters indicates that although 87.35% subjects in Neucardin™ group were with ECG abnormalities at baseline which includes atrial fibrillation (AF), atrioventricular block, premature ventricular contraction, and ST-T changes, these ECG abnormalities were not found to be progressively increased or worsened after Neucardin™ administration. The results show that the QTc of Neucardin™ group of subjects showed a general shortening trend compared with placebo group, and the change of incidence of ventricular arrhythmia and/or ventricular premature beat significantly reduced compared with the placebo group.

The examples listed above do not limit the protection scope of the invention. Without departure from the purposes and scope of the present invention, those of ordinary skill in the art may adjust and change the present invention. Therefore, the protection scope of the invention shall be defined by the claims, rather than by specific examples.

What is claimed:

1. A method for treating ventricular arrhythmias in a mammal in need thereof, comprising administering a polypeptide comprising the epidermal growth factor-like domain of neuregulin-1 (NRG-1) to the mammal.

2. The method of claim 1, wherein the polypeptide comprises the amino acid sequence of SEQ ID NO: 3.

3. The method of claim 2, wherein the mammal is human.

4. The method of claim 1, wherein the polypeptide comprises the amino acid sequence of SEQ ID NO: 2.

5. The method of claim 4, wherein the mammal is human.

6. The method of claim 1, wherein the polypeptide is NRG-1.

7. The method of claim 6, wherein the mammal is human.

8. The method of claim 1, wherein ventricular arrhythmias includes ventricular premature beat (VPB) and/or ventricular tachycardia (VT) and/or ventricular fibrillation (VF).

9. The method of claim 8, wherein ventricular arrhythmia is ventricular premature beat (VPB).

10. The method of claim 9, wherein the mammal is human.

11. The method of claim 8, wherein ventricular arrhythmia is ventricular tachycardia (VT).

12. The method of claim 11, wherein the mammal is human.

13. The method of claim 8, wherein ventricular arrhythmia is ventricular fibrillation (VF).

14. The method of claim 13, wherein the mammal is human.

15. The method of claim 8, wherein the mammal is human.

16. The method of claim 1, wherein the mammal is human.

* * * * *

SEQUENCE LISTING

<160> NUMBER OF SEQ ID NOS: 3

<210> SEQ ID NO 1
<211> LENGTH: 183
<212> TYPE: DNA
<213> ORGANISM: Homo sapiens

<400> SEQUENCE: 1

```
agccatcttg taaaatgtgc ggagaaggag aaaactttct gtgtgaatgg aggggagtgc      60
ttcatggtga aagacctttc aaaccctcg  agatacttgt gcaagtgccc aaatgagttt     120
actggtgatc gctgccaaaa ctacgtaatg gcgagcttct acaaggcgga ggagctgtac     180
cag                                                                    183
```

<210> SEQ ID NO 2
<211> LENGTH: 61
<212> TYPE: PRT
<213> ORGANISM: Homo sapiens

```
<400> SEQUENCE: 2

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 3
<211> LENGTH: 23
<212> TYPE: PRT
<213> ORGANISM: Homo sapiens

<400> SEQUENCE: 3

Ala Glu Lys Glu Lys Thr Phe Cys Val Asn Gly Gly Glu Cys Phe Met
1               5                   10                  15

Val Lys Asp Leu Ser Asn Pro
            20
```